United States Patent
Carney et al.

(10) Patent No.: US 6,602,978 B1
(45) Date of Patent: *Aug. 5, 2003

(54) SYNTHETIC PEPTIDE NEUTROPHIL CELL CHEMOTACTIC AGENTS

(75) Inventors: Darrell H. Carney, Dickinson, TX (US); Shyam Ramakrishnan, Brighton, MA (US)

(73) Assignee: Chrysalis Biotechnology, Galveston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/644,038

(22) Filed: Aug. 22, 2000

Related U.S. Application Data

(63) Continuation-in-part of application No. 08/330,594, filed on Oct. 28, 1994, now Pat. No. 6,184,342.

(51) Int. Cl.[7] .............................................. G50B 19/00
(52) U.S. Cl. ..................................................... 530/300
(58) Field of Search ........................... 424/184.1, 185.1; 530/300, 326, 327, 328, 329; 514/2

(56) References Cited

U.S. PATENT DOCUMENTS

| | | | | |
|---|---|---|---|---|
| 5,256,766 A | * | 10/1993 | Coughlin | 530/327 |
| 5,629,174 A | * | 5/1997 | Sundelin et al. | 435/69.1 |
| 5,688,768 A | * | 11/1997 | Coughlin et al. | 514/15 |
| 5,716,789 A | * | 2/1998 | Sundelin et al. | 435/7.2 |
| 5,759,994 A | * | 6/1998 | Coughlin et al. | 514/9 |
| 5,763,575 A | * | 6/1998 | Sundelin et al. | 530/327 |
| 5,798,248 A | * | 8/1998 | Coughlin et al. | 435/214 |
| 5,849,507 A | * | 12/1998 | Coughlin | 435/7.21 |

FOREIGN PATENT DOCUMENTS

WO  WO 92/14750  *  9/1992

OTHER PUBLICATIONS

Bowie, J.U., et al., "Deciphering the Message in Protein Sequences: Tolerance to Amino Acid Substitutions," *Science* 247:1306–1310, (1990).
Lazar, E., et al., "Transforming Growth Factor α: Mutation of Aspartic Acid 47 and Leucine 48 Results in Different Biological Activities," *Mol Cell Biol* 8(3):1247–1252, (1988).
Burgess, W.H. et al., "Possible Dissociation of the Heparin–binding and Mitogenic Activities of Heparin–binding (Acid Fibroblast) Growth Factor–1 from Its Receptor–binding Activities by Site–directed Mutagenesis of a Single Lysine Residue," *J Cell Biol* 111:2129–2138, (1990).
Accession #P25116, May 01, 1992.*
Accession #A37912, Jan. 22, 1993.*
Burgess et al (J. Cell Bio., 1990, 111:2129–2138.*
Lazar et al (Mol and Cell Biol., 1988, 8:1247–1252).*

* cited by examiner

Primary Examiner—Susan Ungar
(74) Attorney, Agent, or Firm—Hamilton, Brook, Smith & Reynolds, P.C.

(57) ABSTRACT

These compositions are new synthetic peptides and antibodies which are potent chemotactic agents for human neutrophils, and methods for their use. The specificity of these peptides is amino acid sequence specific for binding to a heretofore unidentified receptor on the surface of neutrophils. Neutrophil response to this peptide is specific, since monocytes and fibroblasts do not show any expression of this receptor. Antibodies against these peptides block the chemotactic response. Such antibodies are useful to modulate neutrophil recruitment to a wound site for enhancing or inhibiting inflammation and early effects of wound healing.

2 Claims, 6 Drawing Sheets

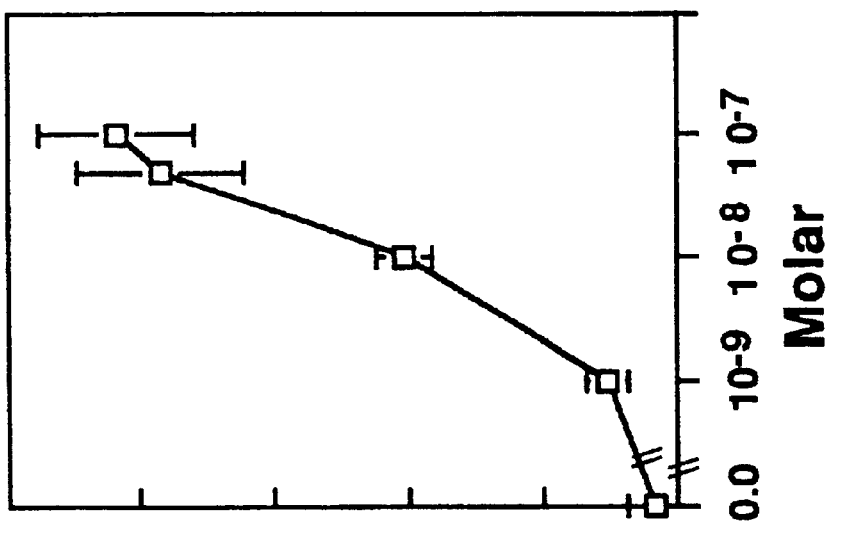
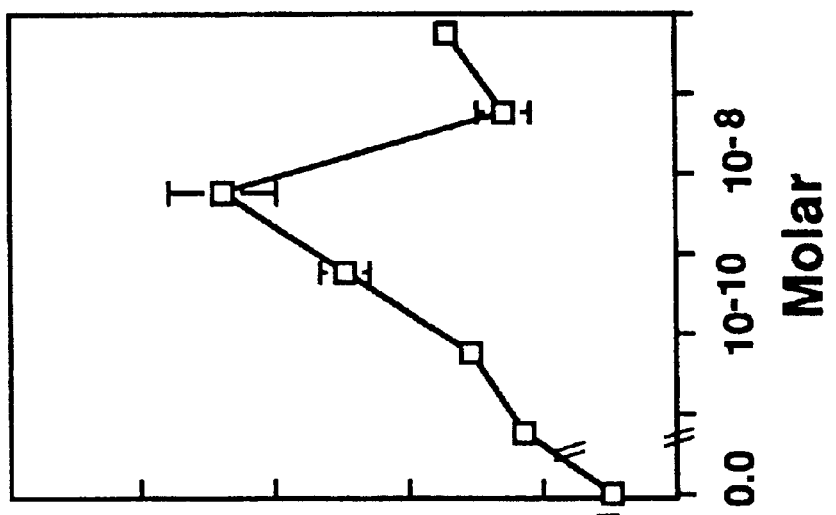

SEQUENCE LISTING

<160> NUMBER OF SEQ ID NOS: 9

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 1

Arg Arg Pro Glu Ser Lys Ala Thr Asn Ala Thr Leu Asp Pro Arg
 1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 2

Arg Gln Pro Glu Ser Glu Met Thr Asp Ala Thr Val Asn Pro Arg
 1               5                   10                  15

<210> SEQ ID NO 3

```
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Ser Gln Pro Glu Ser Glu Arg Thr Asp Ala Thr Val Asn Pro Arg
 1               5                  10                  15

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Arg Gln Pro Glu Ser Glu Arg Met Tyr Ala Thr Pro Tyr Ala Thr Pro
 1               5                  10                  15

Asn Pro Arg

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Cys Arg Gln Pro Glu Ser Glu Met Thr Asp Ala Thr Val Asn Pro Arg
 1               5                  10                  15

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Tyr Arg Arg Pro Glu Ser Lys Ala Thr Asn Ala Thr Leu Asp Pro Arg
 1               5                  10                  15

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Ser Phe Leu Leu Arg Asn Pro Asn Asp Lys Tyr Glu Pro Phe
 1               5                  10

<210> SEQ ID NO 8
<211> LENGTH: 23
<212> TYPE: PRT
<213> ORGANISM: Artificial Sequence
<220> FEATURE:
<223> OTHER INFORMATION: Description of Artificial Sequence: Synthetic
      Peptide
```

```
-continued

<400> SEQUENCE: 8

Ala Gly Tyr Lys Pro Asp Glu Gly Lys Arg Gly Asp Ala Cys Glu Gly
 1               5                  10                  15

Asp Ser Gly Gly Pro Phe Val
            20

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Ser Phe Phe Leu Arg Asn
 1               5
```

SYNTHETIC PEPTIDE NEUTROPHIL CELL CHEMOTACTIC AGENTS

RELATED APPLICATIONS

This application is a continuation-in-part of co-pending U.S. Ser. No. 08/330,594 filed Oct. 28, 1994, now U.S. Pat. No. 6,184,342 the entire teachings of which are incorporated herein by reference.

BACKGROUND OF THE INVENTION

The U.S. Government has a paid-up non-exclusive license in this invention, and may have other rights as stipulated in 35 U.S.C. § 202(C)

1. Field of the Invention

The present invention relates generally to the fields of protein biochemistry, protein sequences, drugs and therapeutics. More specifically, the present invention relates to peptides and antibodies useful for modulated neutrophil chemotaxis response in the immune response and in wound healing.

2. Description of Related Art

An enzyme in blood (thrombin) plays an important role in the inflammatory process and in initiating early stages of wound healing (Carney 1992; Carney et al. 1992b) by stimulating a number of cellular events which increase vascular permeability and recruit inflammatory cells to the site of tissue injury. It activates platelets and stimulates proliferation of fibroblasts (Carney et al. 1978; Perez-Rodriguez et al. 1981), capillary endothelial cells (Belloni et al. 1992), epithelial cells (He et al. 1991), neuronal cells (Gurwitz and Cunningham 1988), monocytes (Bar-Shavit et al. 1986), and T cells (Naldini et al. 1993.). Additionally, a thrombin-derived synthetic peptide, TRAP-508, accelerates wound healing and revascularization through mechanisms that mimic normal effects of thrombin on microvascular endothelial cells and the recruitment of inflammatory cells tro the wound site in vivo (Carney et al. 1992a; Stiernberg et al 1993). However, the mechanisms by which this enzyme and related synthetic peptides stimulate these cellular events are quite complex and not generally understood.

It is highly useful for research and clinical purposes to have available the biochemical factors which mediate the various mechanisms that regulate the wound healing and inflammation processes. Neutrophil cell chemotaxis initiated by thrombin is one such mechanism involved in the wound healing/inflammation response process about which more needs to be known.

What is known about these processes is that thrombin and thrombin peptides play a role in chemotactic recruitment of inflammatory cells, including neutrophils (a.k.a. polymorphonuclear leucocytes) to a wound site. Further, it is known that at the injury site, thrombin causes proteolytic cleavage and activation of a G-protein-linked Proteolytically Activated Receptor for Thrombin (PART) that is present on the surface of platelets and endothelial cells (Vu et al. 1991; Rasmussen et al 1991; Zhong et al. 1992), which results in release of an N-terminal peptide of approximately 15-amino acids.

However, prior to the present invention, the fate of this N-terminal peptide cleavage fragment was not known, nor was there any known function or use for this peptide fragment. Tests on fibroblasts and other cells using the released N-terminal peptide had found no apparent activity of the released peptide (Van Obberghen-Schilling and Pouyssegur 1993).

SUMMARY OF THE INVENTION

The present invention embodies synthetic peptides which are neutrophil cell chemotactic agents, and which mimic the activity and role of the cleavage fragment of the Proteolytically Activated Receptor for Thrombin (PART). The benefits of these agents and the antibodies to them is their utility in research and clinical applications for studying and enhancing aspects of the wound healing and inflammatory response processes.

An object of the present invention is a number of peptides that are useful as chemotactic agents for cells having a receptor for the Neutrophil Targeting Peptide (NTP): SEQ. ID NO:1, SEQ. ID NO:2, SEQ. ID NO:3, and SEQ. ID NO:4 (see Table 1). This object also embodies peptides comprising a series of at least seven amino acids of any of SEQ. ID NO:1, SEQ. ID NO:2, SEQ. ID NO:3, and SEQ. ID NO:4. A further aspect of this object is that these peptides are capable of specific binding to an NTP receptor on neutrophil cells generally, and to an NTP receptor on human neutrophil cells in particular.

Another object of the present invention is a process of stimulating neutrophil cell chemotactic migration by forming a gradient of a peptide of the present invention in an environment in which neutrophil cells are present or otherwise available, e.g., recruitable from the circulation in an in vivo system. The gradient may be accomplished by adding at a site in the environment toward which the neutrophil cells are to migrate an effective amount of the peptide sufficient to establish a gradient of the peptide against which the neutrophil cells migrate. It is a particular aspect of this process where the neutrophil cells are human neutrophil cells. The amount of the peptide to be added at the site can be any amount that one skilled in the art would recognize as establishing the required peptide gradient. However, it is a further aspect of this embodiment that the added amount of peptide is equivalent to a concentration of about $10^{-10}$ to $10^{-4}$ Molar in the area of the addition.

An additional object of this invention is a process of generating antibodies using as an antigen a series of amino acids defined by SEQ. ID NO: 1, SEQ. ID NO:2, SEQ. ID NO:3, SEQ. ID NO:4, and SEQ. ID NO:5 and the products of that process. Specifically, the polyclonal antibody pAb51-IgG anti-NTP is an embodiment of this object.

A further object of the present invention is a process of modulating neutrophil cell chemotactic migration by adding antibodies of the present invention at a site in the system at which neutrophil migration is to be modulated in an amount effective to modulate the neutrophil cell migration. It is a further aspect of this embodiment that the added amount of the peptide is equivalent to a concentration of about $10^{-10}$ to $10^-$Molar in the area of the addition.

It is also an object of this invention that the compositions and processes be accomplished both in vivo and in vitro.

TABLE 1

| PEPTIDE SEQUENCES | | |
| --- | --- | --- |
| Sequence | Source | Amino Acid Sequence |
| SEQ. ID NO:1 | Human | +N-RRPESKATNA TLDPR |
| SEQ. ID NO:2 | Hamster | +N-RQPESEMTDA TVNPR |
| SEQ. ID NO:3 | Mouse | +N-SQPESERTDA TVNPR |
| SEQ. ID NO:4 | Rat | +N-RQPESERMYA TPYATPNPR |
| SEQ. ID NO:5 | Hamster | +N-CRQPESEMTDA TVNPR |

BRIEF DESCRIPTION OF THE DRAWINGS

FIG. 1A Effect of alpha-thrombin on neutrophil cell chemotaxis.

FIG. 1B Effect of DIP-inactivated thrombin on neutrophil cell chemotaxis.

FIG. 1C Effect of Interleukin-8 on neutrophil cell chemotaxis.

DESCRIPTION OF THE PREFERRED EMBODIMENTS

Materials

Figure 2:
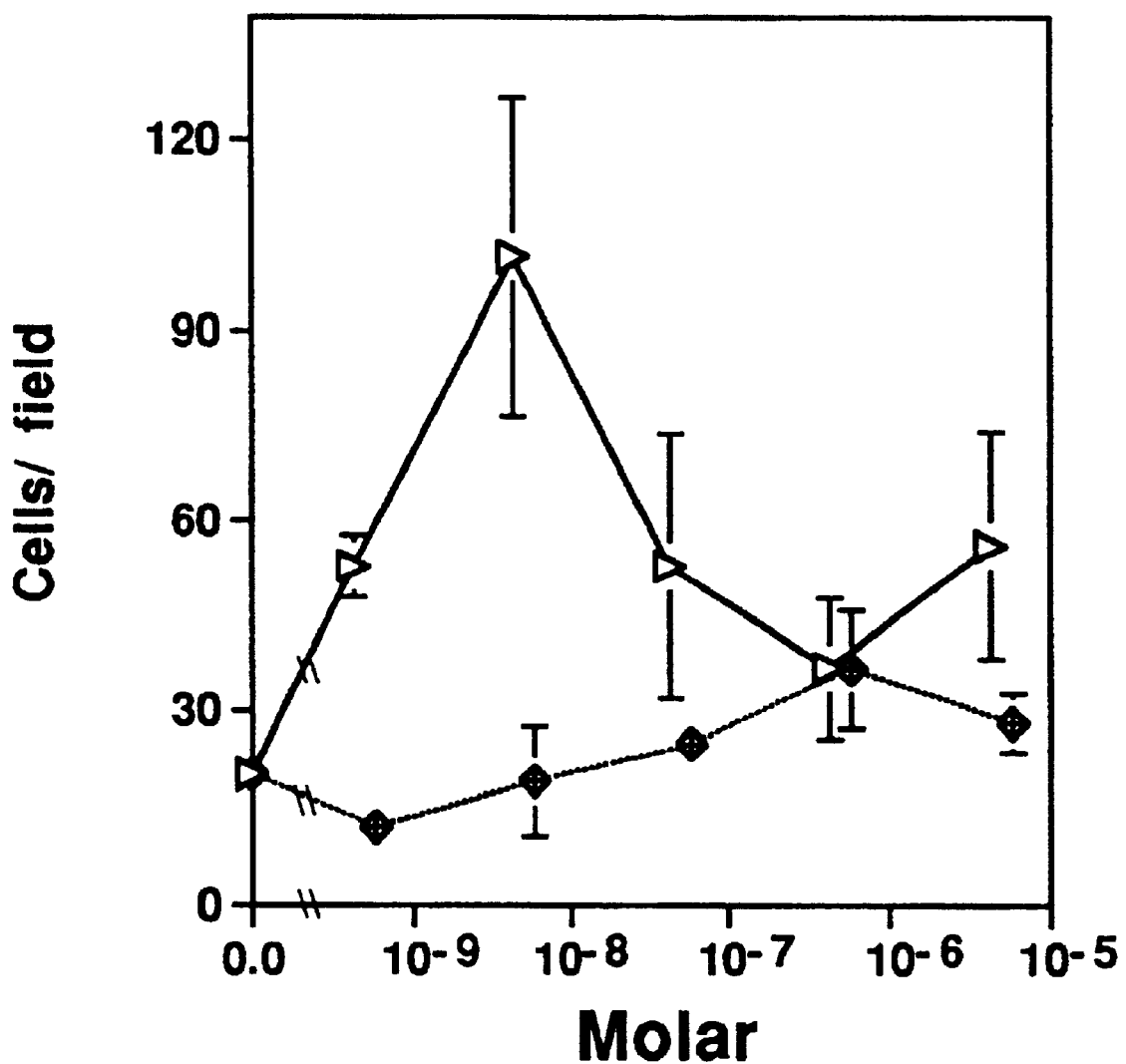
FIG. 2 Effect of PART activating peptide (♦) and the thrombin-derived high-affinity receptor binding peptide, TRAP-508 (➤) on human neutrophil cell chemotaxis.

The peptides of the present invention were synthesized on a MILLIGEN BIOSEARCH AUTOMATED PEPTIDE SYNTHESIZER®, model 9600, using t-boc chemistry. Ficoll Hypaque (MONO POLYRESOLVING MEDIUM™) was obtained from ICN Hiomedicals (costa Mesa, Calif.). Dulbecco-Vogt Modified Medium (DMEM), Ham's F-12, and powdered Hanks Balanced Salt Solution (HBSS) were obtained from Gibco (Grand Island, N.Y.). DIFF-QUIK® staining kits were obtained from Baxter Scientific Products (Houston, Tex.). Multiwell chemotaxis chambers and 3.0 μM NUCLEOPORE™ PVP-free filters were obtained from Neuro Probe (Cabin John, Md.). Whatman GF/C filters from Millipore were used in the receptor binding assays. Other reagent grade chemicals were obtained from Sigma Chemical Co. (St. Louis, Mo.) except as noted.

Cells

Human neutrophils were isolated from blood of healthy volunteers, drawn into one-tenth volume of trisodium citrate. The neutrophils were isolated from the blood using established Ficoll-Hypaque (MONO POLYRESOLVING MEDIUM™) protocol, Kalmer et al. 1988, specifically incorporated hereinby reference. The cells were washed in HBSS containing 20 mM HEPES, pH (7.4 (HHBSS), pelleted by centrifugation (600 x g), and resuspended into HUBSS at the indicated density. Trypan blue exclusion assays indicated greater than 97% cell viability.

Chemotaxis using multiwell chambers

Freshly isolated human neutrophils (150,000 cells per 50 μl) were applied to wells of Modified Boyden 48-well Microchemotaxis Chambers (Neuro Probe, Cabin John, Md.) with pre-wet 3.0 mM, PVP-free polycarbonate membranes (Neuro Probe, Cabin John, Md.) (Mansfield, et al. 1990, which is specifically incorporated herein by reference). The lower wells in these chambers were filled with 27 μl of HHBSS solution containing indicated concentrations of substances to be tested. After loading, the chambers were incubated for 2 hours at 37° C. Membranes were removed, rinsed with HHBSS, fixed and stained using DIFF-QUIK® to visualize and quantitate cells that had migrated through the filters. For each assay condition, cells migrating through 4 wells were examined using a Nikon Microscope (at 400x). For each well, the total cells present in 6 random fields were counted and recorded. Each assay represents data from at least three analyses of the same type with neutrophils isolated from at least two individuals.

Generation of Polyclonal Antibody pAb51.

A peptide representing the 15-amino acid fragment released from PART (residues 26–41), with addition of N-terminal cysteine (CRQPESEMTDATVNPR-NH$_2$; SEQ ID NO:5) was synthesized, and purified by reverse phase high performance liquid chromatography. This peptide was conjugated to SUPER CARRIER® cationized bovine serum albumin (Pierce, Rockford, Ill.), in which the carboxyl groups were blocked to produce a protein with a basic p1, while the amino groups were modified through the NHS-ester end of the heterobifunctional crosslinker, sulpho-SMCC (Harlow and Lane, 1988, specifically incorporated herein by reference). The peptide conjugate was mixed with aluminum hydroxide adjuvant suspension (IMJECT ALUM®, Pierce, Rockford, Ill.), injected intradermally into six to ten sites (approximately 0.1–0.2 ml per site, total of 800 μg of antigen) per rabbit (New Zealand White males). Rabbits were housed and cared for in an approved animal care facility using protocols approved by an institutional animal care and use committee. Six weeks after the initial immunization, the rabbits were boosted with the same conjugate suspension and the serum was collected at two week intervals, for six weeks. IgG fractions were purified from fresh or frozen serum using AVID AL™ columns (Bioprobe International, Inc., Tustin, Calif.).

Iodination of NTP

NTP was radiolabeled using IODO-GEN® (Pierce) catalyzed iodination (Fraker and Speck, 1978, which is specifically incorporated herein by reference). 5 mCi of Na$^{125}$I (Amersham UK) was incubated in glass tubes coated with IODO-GEN® with 250 μg of HPLC-purified NTP-Y in 250 μl of Phosphate Buffered Saline (PBS), pH 7.2. After 7 minutes, the radiolabeled peptide was separated from free $^{125}$I by its adsorption to a C-18 SEP PAK® column, followed by elution with 100% acetonitrile. The eluted radioactive peptide was then dried under vacuum to remove acetonitrile, rehydrated with PBS, and stored as frozen aliquots (−20° C.) at a concentration of 10 μg/ml.

NTP binding assays.

To determine if NTP exhibited specific binding to neutrophils, binding studies were done with $^{125}$I-NTP-Y. Because peptides are highly susceptible to proteolytic degradation, binding was done in the presence of 1 μg/ml of nonspecific peptide, to dilute out the effect of proteases and sodium azide (0.02%) was added to prevent internalization and degradation.

For saturation binding assays, 1×10$^{-6}$ neutrophils were incubated at 37° C. with indicated concentrations of $^{125}$I-NTP-Y in 100 μl of DV medium containing 20 mM HEPES buffer, pH 7.4, in 0.6 ml eppendorf tubes. The binding was terminated and $^{125}$I-NTP-Y that was bound to cells was separated from free $^{125}$I-NTP-Y by rapid filtration and rinsing (2 X with 10 mls of 4° C. PBS) through Whatman GF/C filters, using a Millipore filtration apparatus. Radioactivity on filters was then counted in a gamma counter (Beckman Instruments, Inc., model Gamma 4000). Nonspecific binding of $^{125}$I-NTP-Y was measured in the presence of a 500-fold molar excess of unlabeled peptide and was subtracted from total binding to determine the amount of specific (saturable) binding.

Assay for Superoxide Generation by NTP-Stimulated Neutrophils

Superoxide generation was determined by measuring the superoxide dismutase (SOD)-inhibitable reduction of ferricytochrome C (Thomas et al, 1992, incorporated herein by reference). Briefly, $2\times10^6$ neutrophils/ml were incubated with, ferricytochrome C (433 $\mu$g/ml) and glucose (1.1 mM) in phosphate buffered saline (PBS) at 37° C. for five minutes, in presence or absence of 1 $\mu$g/ml SOD. Twenty minutes after addition of NTP, IL-8, or PBS, aliquots were removed, cooled to 4° C., and filtered through 0.45 $\mu$M particle separators (Amicon). The optical absorption of the filtrate was then read at 550 nm. The amount of $O_2$ generated was calculated by the difference in absorbance of the samples with or without SOD, using a 15.5 millimolar extinction coefficient at 550 nm for cytochrome C reduction.

Superoxide generation induced by 800 nM NTP was equivalent to only 9±0.9 nmoles of $O_2$ released, whereas, 400 nmolar IL-8 generated release of 102±16 nmoles of $O_2$. Therefore, superoxide generation by NTP is negligible compared to IL-8. Thus, NTP may be primarily involved in initial chemoattraction of neutrophils to the site of the wound where they adhere to activated endothelial cells and move into the wounded tissue. This characteristic of NTP distinguishes it from other chemotactic agents which stimulate superoxide production associated with potential tissue damage.

The following examples are intended as illustrations of the practice of this invention and are not meant to limit the scope of the invention. One skilled in the art in view of this disclosure will be able to practice this invention using equivalent materials and methods of his/her own preference.

EXAMPLE 1

Thrombin Substrate and Pathway Role in Chemotaxis

FIG. 1 demonstrates the effect of α-thrombin, DIP-inactivated thrombin, and Interleukin-8 on neutrophil chemotaxis. Freshly isolated human peripheral blood neutrophils were added to wells of Modified Boyden Microwell Chemotaxis Chambers and the number of cells migrating through the filters was determined as described in Materials and Methods. For each assay, cells migrating through 4 wells were examined, counted, and recorded (6 random fields per well) using a Nikon LabPhot Microscope (400x).

As shown in FIG. 1, proteolytically active thrombin and DIP-inactivated thrombin both stimulated neutrophil chemotaxis. Maximal stimulation for active α-thrombin (FIG. 1A) and DIP-inactivated thrombin (FIG. 1B) appears to require concentrations betwen 2 and 200 ng per ml ($5.5\times10^{-11}$M to $5.5\times10^{-9}$M). The magnitude of stimulation by thrombin and DIP-thrombin stimulation was comparable to the stimulation observed with recombinant IL-8 (FIG. 1C). Half-maximal stimulation required an IL-8 concentration of $\sim10^{-8}$M, but required only $\sim3^{-10}$M DIP-thrombin, or $3\times10^{-1}$M α-thrombin. Therefore, both DIP-thrombin and native 60 -thrombin were much more potent chemotaxins than IL-8. Control wells had fewer than 20 cells per field migrating through the filters.

This example demonstrated that stimulation of migration is directed chemotaxis and not simply chemokinetic activation of the cells, and that the thrombin pathway was an influencing aspect of the mechanism. Further demonstrated was that thrombin stimulated chemotaxis did not require proteolytic activity.

EXAMPLE 2

Thrombin and Thrombin Receptor Peptide Fragment Stimulation of Chemotaxis

FIG. 2 shows the effect of PART activating peptide and the thrombin-derived peptide fragment, TRAP-508, on neutrophil chemotaxis. Human neutrophils were added to wells of Boyden Microwell Chambers and assayed for directed chemotaxis toward indicated concentrations of synthetic peptides representing the tethered ligand region of PART (SFLLRNPNDKYEPF—SEQ ID NO. 7), or TRAP-508, the high-affinity receptor binding domain of human thrombin (AGYKPDEGKRGDACEGDSGGPFV—SEQ ID NO.8).

FIG. 2 demonstrates that concentrations of PART activating peptide fragment up to 7.0 $\mu$M were only marginally chemotactic for neutrophils (FIG. 2A). This same PART activating peptide fragment preparation stimulated c-fos and other G-protein initiated signals in fibroblasts to nearly the same extent as proteolytically active thrombin. Therefore, the PART activating peptide fragment was not sufficient to stimulate chemotaxis. This result was supported by art indicating the neutrophils did not express the PART receptor component (Howells et al., 1993; Hoffman and Church, 1993).

In contrast to the lack of effect observed after addition of the PART activation peptide, addition of the thrombin peptide fragment, TRAP-508, in nanomolar concentrations stimulated chemotaxis to approximately the same extent as seen with intact thrombin or IL-8 (FIG. 2). This confirms that neutrophil chemotaxis were stimulated by non-proteolytic interaction of a thrombin peptide fragment. This direct chemotactic effect of thrombin peptide fragment, TRAP-508, on neutrophil cells was in line with the acceleration of wound healing elicited by TRAP-508 peptide fragment in vivo (Vu et al., 1991; Stiernberg et al., 1993), and the binding of this TRAP-508 peptide to specific receptors on cells (Glenn et al., 1988). Directly stimulating chemotaxis in neutrophils using the TRAP-508 peptide demonstrates the feasibility of successfully using peptide fragments to mimic normal activity in vivo in the thrombin pathway. Since TRAP-508 peptides stimulated neutrophil chemotaxis and enhanced wound healing, therefore the present peptides in view of their stimulation of neutrophil chemotaxis should similarly influence wound healing.

EXAMPLE 3

Figure 3:
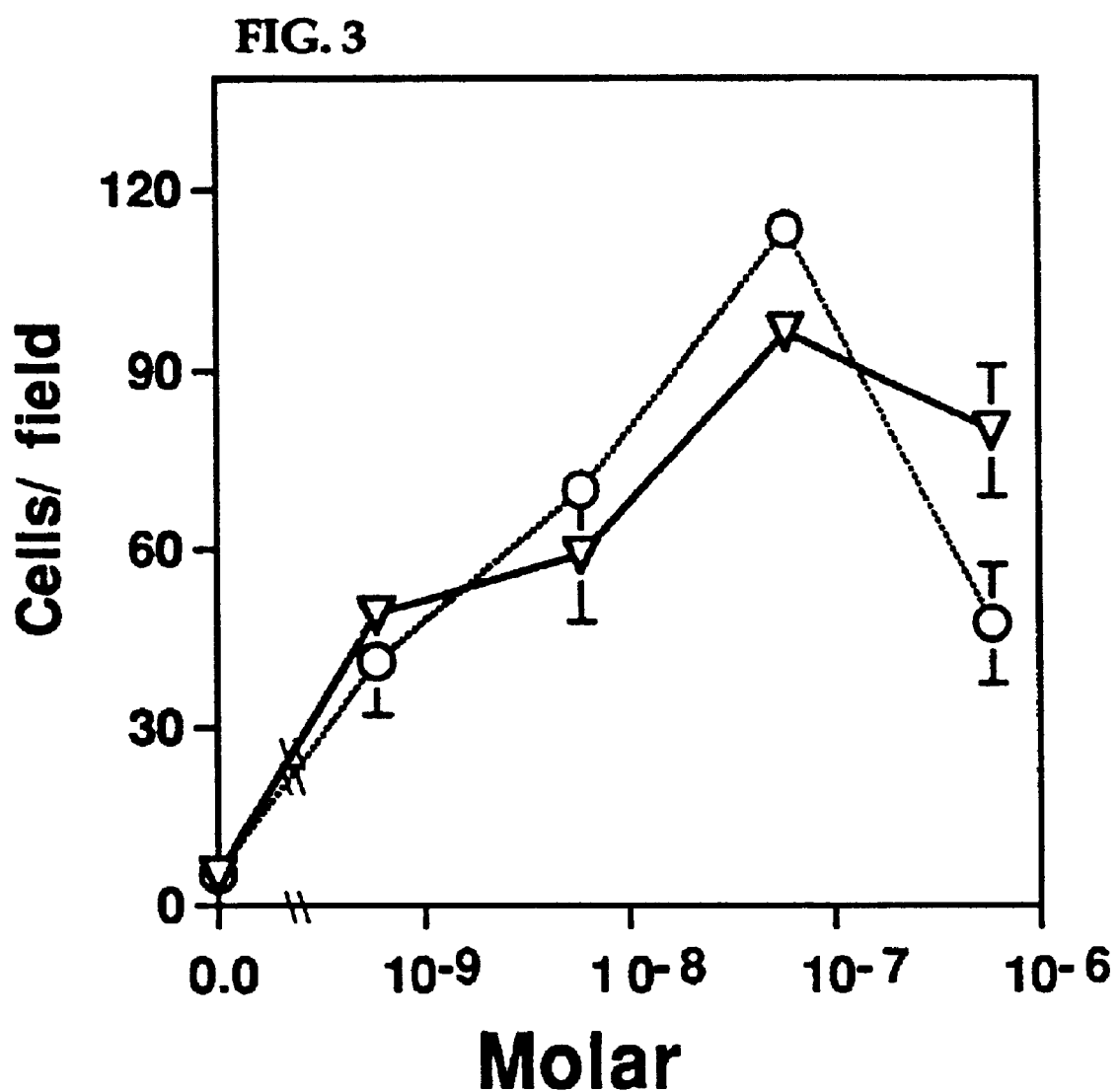
FIG. 3 Effect of hamster (○) and human (▽) Neutrophil Targeting Peptide (NTP) on neutrophil cell chemotaxis.

Chemotactic and Targeting Function of the N-terminal Peptide Cleavage Fragment of PART FIG. 3 shows the effect of Neutrophil Targeting Peptide (NTP) on neutrophil chemotaxis. Indicated concentrations of peptides representing residues 26–41 of the human (SEQ ID NO:1) (▽) or hamster (SEQ ID NO:2) (○) PART receptor component were added to lower wells of Boyden Microwell Chambers and neutrophil chemotaxis toward the peptides was assayed as described above.

Thrombin activation of platelets and endothelial cells at an injury site involves the proteolytic cleavage of PART, with the release of an N-terminal peptide fragment referred to as PART activation peptide (Vu et al., 1991). Therefore, release of the PART activation peptide is an end result of thrombin binding and proteolytic cleavage of PART. The non-proteolytic effect of the synthetic TRAP-508 peptide or DIP-thrombin are mediated through direct interaction with the high-affinity binding site as an event directly preceding cleavage of PART and release of the PART activation peptide.

FIG. 3 demonstrates that peptides representing the released N-terminal fragment of both hamster and human PART are potent chemotaxins for neutrophils in Boyden microwell chemotactic assays. As shown, these peptides were chemotactic at concentrations ranging from 1 to 200 ng/ml with maximal stimulation nearly equivalent to that seen with thrombin or IL-8 (FIG. 1C). The released N-terminal fragment peptide acted as a chemotactic agent targeted at neutrophils to stimulate their migration to a site of injury and thrombin production, and is herein called a Neutrophil Targeting Peptide (NTP). As with thrombin-stimulated migration, control assays did not demonstrate stimulation of neutrophil migration.

EXAMPLE 4

Specificity of Neutrophil Chemotaxis Stimulated by NTP and Antibody Modulation

Figure 4:
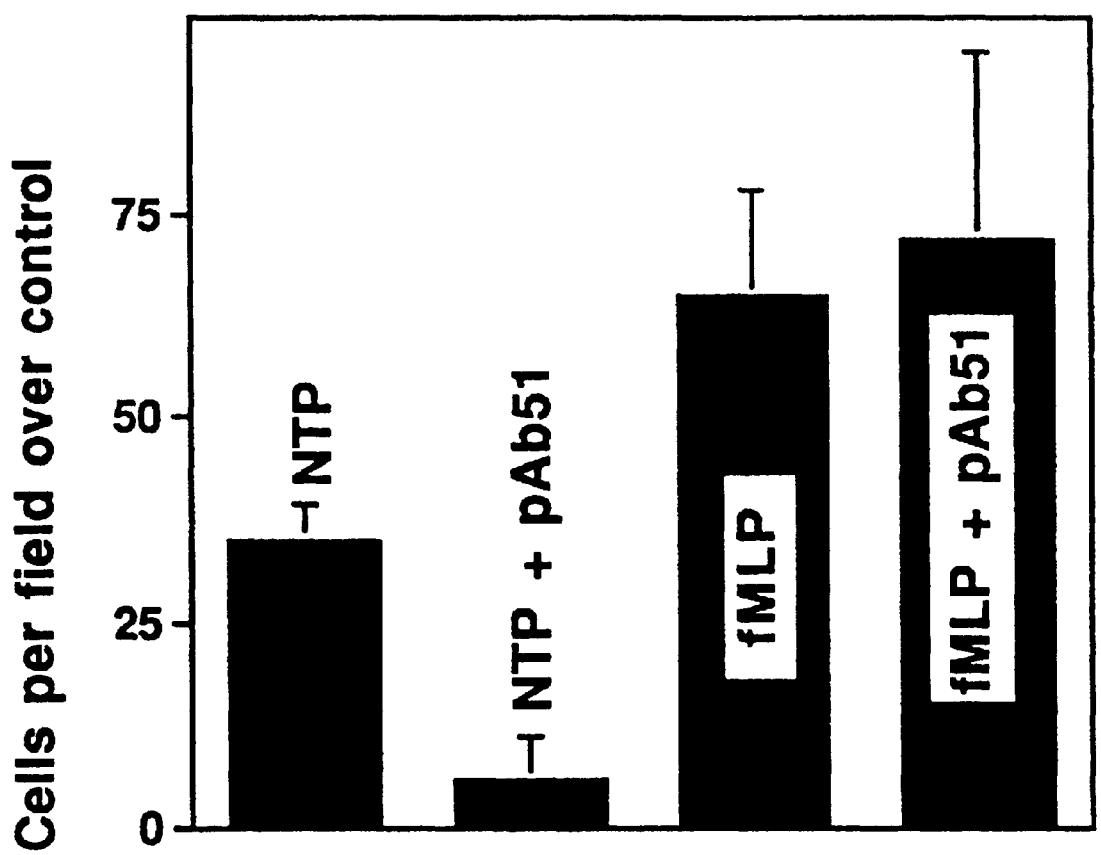
FIG. 4 Effect of pAb51-IgG anti-NTP polyclonal antibody on chemotactic migration stimulated by NTP or fMet-Leu-Phe.

FIG. 4 demonstrates the effect of pAb51-IgG anti-NTP polyclonal antibody on chemotaxis stimulated by NTP of fNet-Leu-Phe. pAb51-IgG anti-NTP antibodies were raised against the NTP peptide synthesized with a N-terminal cysteine residue (CRQPESEMTDATVNPR-$NH_2$, SEQ ID NO:5) and purified as described in Methods. pAb51-IgG anti-NTP IgG (50 $\mu$g/ml) was incubated with NTP (100 ng/ml), or f-Met Leu Phe (50 ng/ml) for 4 hr and the chemotactic effects of these peptides were determined as described above.

NTP stimulated neutrophil chemotaxis while other peptides such as the (SFFLRN—SEQ ID NO. 9) peptide at concentrations up to 2000-fold higher did not. This indicated a specific interaction of NTP with neutrophils. 50 $\mu$g/ml of pAb51-IgG anti-NTP antibodies was incubated with NTP and with fMet Leu Phe prior to their application into the lower wells of the microwell chambers. Specific chemotaxis stimulated by NTP (above that observed in pAb51-IgG controls) was almost completely inhibited in the presence of antibody, while that stimulated by fMet Leu Phe was not affected (see FIG. 4).

EXAMPLE 5

Specific NTP Receptor on Human Neutrophil Cells

Figure 5:
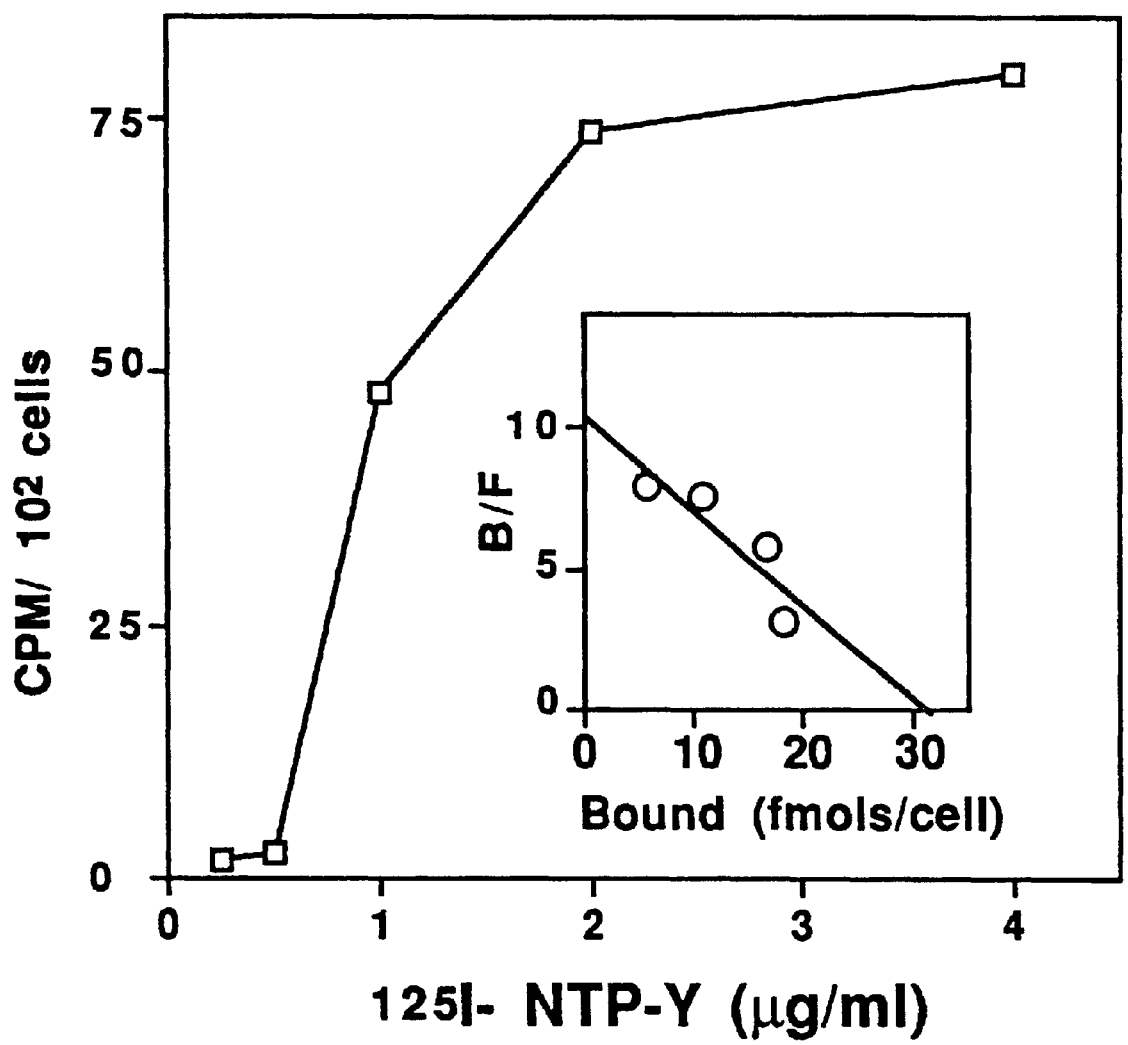
FIG. 5 Specific binding of $^{125}$I-labeled NTP-Y to human neutrophils.

FIG. 5 demonstrates binding of $^{125}$I-labeled NTP-Y to human neutrophils. NTP was synthesized with an N-terminal tyrosine (YRRPESKATNATLDPR—SEQ ID NO. 6), analyzed for chemotactic activity, and radiolabeled as described in Methods. Indicated concentrations of $^{125}$I-labeled NTP-Y were added to $1\times10^6$ neutrophils in 100 $\mu$l of binding medium (Delbecco-Voght modified medium containing 20 mM HEPES buffer, pH 7.4, containing 1 $\mu$g/ml of nonspecific peptide to help prevent degradation of $^{125}$I-labeled NTP-Y), and 0.02% sodium azide (to prevent internalization) and incubated 45 min at 37° C. Binding was terminated and filters processed as described in Methods. Specific binding was determined by subtracting the nonspecific binding of $^{125}$I-NTP-Y (binding in the presence of 500-fold molar excess of unlabeled NTP-Y) from the total binding. Insert represents a Scatchard-like analysis of the binding isotherm using total radioactivity in the medium as a measure of free ligand. The data are representative of three sets of experiments performed on different days with neutrophils isolated from two donors.

Binding assays with iodinated-NTP-Y demonstrated a dose-response curve nearly identical to NTP indicating that iodination does not alter peptide activity. $^{125}$I-NTP-Y binding (40 min at 37° C.) was specified and saturable (FIG. 5). This demonstrated the presence of a specific receptor binding site for NTP. The saturation curve and Scatchard-like analysis of this binding data (FIG. 5-Insert) demonstrated the presence of ~3000 NTP receptors per cell. The chemotactic effects of NTP appeared to be mediated by interaction with specific NTP receptor binding sites on the surface of neutrophils. Parallel binding studies with fibroblasts showed no detectable specific binding of $^{125}$I-NTP-Y, indicating that this receptor was not present on fibroblasts.

EXAMPLE 6

Gradient Formation and Neutrophil Chemotaxis

Figure 6A:
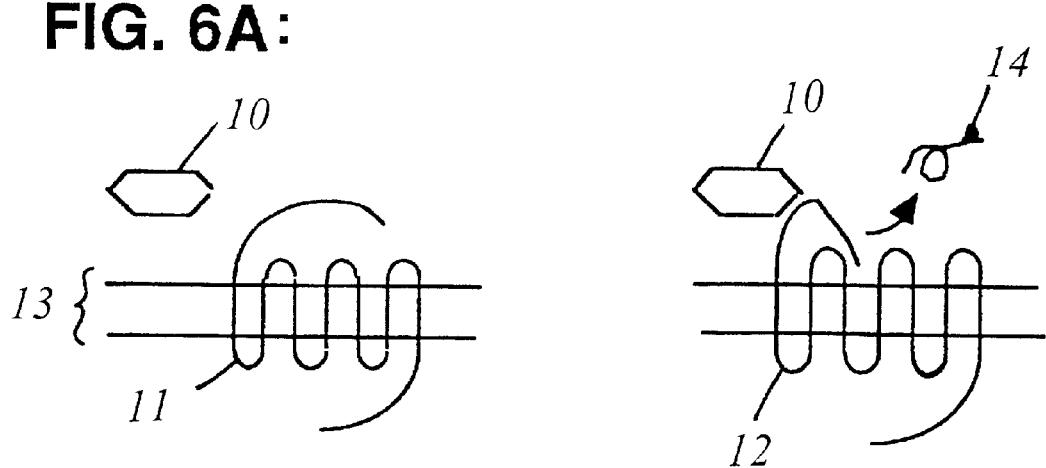
FIG. 6A Depicts thrombin cleavage of the PART receptor on cells at the site of vascular injury, releasing NTP to establish a gradient that targets neutrophils to the site of the injury.
Figure 6B:
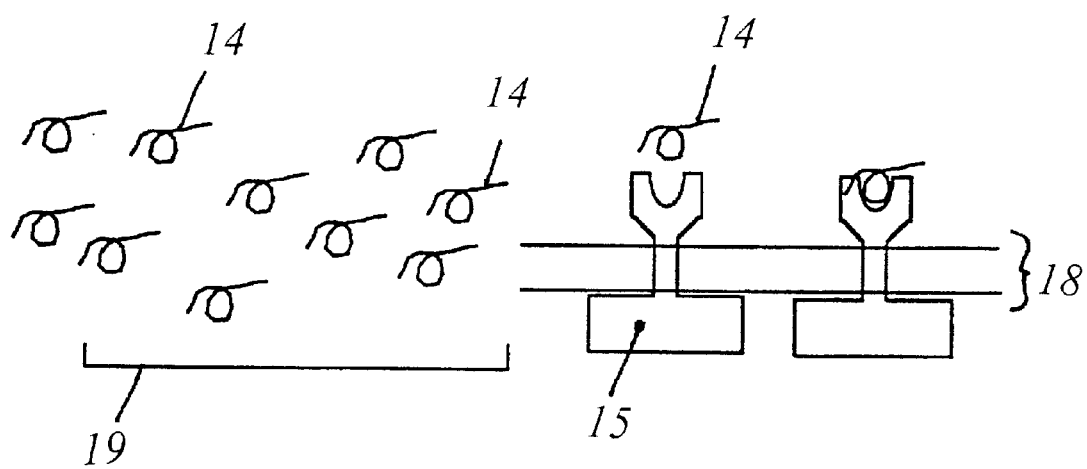
FIG. 6B Depicts NTP initiating chemotaxis by binding and interacting with specific NTP receptors on the surface of neutrophils.
Figure 6C:
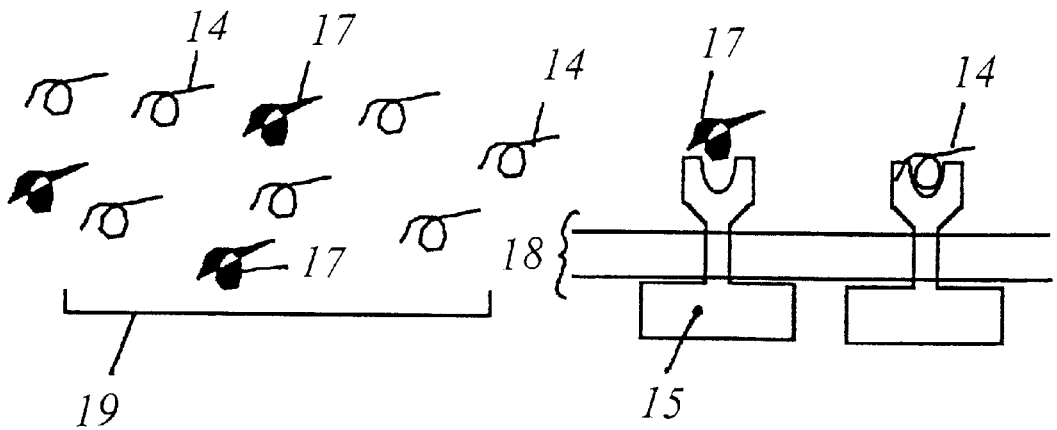
FIG. 6C Depicts how activation of the normal neutrophil chemotaxis at an injury site may be accomplished using application of a present synthetic peptide to mimic or supplement the gradient normally occurring due to thrombin cleavage of the PART receptor.

FIG. 6A depicts a proteolytically active thrombin molecule 10 interacting with a Proteolytically Activated Receptor for Thrombin (PART) 11 at the cell membrane 13 of platelets and endothelial cells at an injury site. After binding, the thrombin molecule 10 cleaves the PART 12 and releases a Neutrophil Targeting Peptide (NTP) 14. This demonstrates how thrombin cleavage of PART receptor component on the surface locally releases NTP at a vascular injury site. FIG. 6B depicts a gradient 19 of NTP molecules is formed as numerous thrombin/PART interactions locally release numerous NTP molecules at an injury site. Dispersion of NTP molecules from the injury site forms a gradient 19 of NTP peptides 14 (left side of figure). The right side of the figure depicts how an NTP 14 peptide interacts with a chemotactic receptor 15 on a neutrophil cell membrane 18 in a receptor specific manner, to stimulate the neutrophil to migrate up the gradient 19 to the left. Together, FIG. 6A and FIG. 6B demonstrate how neutrophils are recruited to the site of a tissue injury by thrombin cleavage of PART and by direct interaction of NTP peptides with neutrophil receptors specific for these peptides. FIG. 6C depicts how a synthetic peptide chemotactic agent 17 of the present invention can operate in a manner similar to native NTP 14 to either help establish a gradient 19 or compete for binding at the receptor 15. If the synthetic peptide chemotactic agent 17 mimics the NTP molecule's activity as an agonist, then NTP activity is enhanced. If the synthetic peptide chemotactic agent 17 binds, but does not mimic the NTP molecule's activity, it acts as an antagonist, and the NTP activity is diminished. Therefore, the synthetic peptide chemotactic agent of this invention may act to positively or negatively modulate neutrophil chemotactic activity.

REFERENCES

Bar-Shavit, Kahn, Mann and Wilner, "Identification of a thrombin sequence with growth factor activity on macrophages," *Proc. Natl. Acad. Sci. USA* 83:976, 1986.

Belloni, Carney and Nicolson, "Isolation and partial characterization of murine and human endothelial cells from various organs: Differential responsiveness to thrombin and other growth factors," *Microvas. Res.* 43:20, 1992

Carney, Glenn and Cunningham. "Conditions which affect initiation of animal cell division by trypsin and thrombin." *J. Cell. Physiol.* 95:13. 1978.

Carney, Mann, Redin, Pernia, Berry, Heggers, Hayward, Robson, Christie, Annable, Fenton II and Glenn, "Enhancement of incisonal wound healing and neovascularization in normal rats by thrombin and synthetic thrombin receptor-activating peptides," *J. Clin. Invest.* 89:1469, 1992a.

Carney, Redin and McCroskey, "Role of high-affinity thrombin receptors in postclotting effects of thrombin," *Semin. Thromb. Hemost.* 18:91, 1992b.

Carney, "Postclotting cellular effects of thrombin mediated by interaction with high-affinity thrombin receptors, In *Thrombin Structure and Function*, ed. L. Berliner, New York, p. 351, 1992.

Fraker and Speck, "Protein and cell membrane iodinations with a sparingly soluable chloramide 1,3,4,6-tetrachloro-3,6-diphenylglycoluril," *Biochem. Biophys. Res. Comm.,* 80(4):849–857. 1978.

Glenn, Frost, Bergmann and Carney, "Synthetic peptides bind to high-affinity thrombin receptors and modulate thrombin mitogenesis," *Peptide Res.* 1:65, 1988.

Gurwitz and Cunningham, "Thrombin modulates and reverses neuroblastoma neurite outgrowth," *Proc. Natl. Acad Sci. USA* 85:3440, 1988.

Harlow and Lane, *Antibodies: a laboratory manual*, Cold Spring Harbor Laboratory, Cold Spring Harbor, New York, p. 726, 1988.

He, Rondeau, Medcalf, Lacave. Schleuning and Sraer, "Thrombin increases proliferation and decreases fibrinolytic activity of kidney glomerular epithelial cells," *J. Cell. Physiol.* 146:131, 1991.

Hoffman and Church, "Response of blood leukocytes to thrombin receptor peptides," *J. Leukoc. Biol.* 54:145, 1993.

Howells, Macey, Curtis and Stone, "Peripheral blood lymphocytes express the platelet-type thrombin receptor," *Br. J Haematol.* 84:156, 1993.

Kalmer, Arnold, Warbington and Gardener. "Superior leukocyte separation with a discontinuous one-step Ficoll-Hypaque gradient for the isolation of human neutrophils," *J. Immunol. Meth.* 110:275, 1988.

Mansfield, Boxer and Suchard, "Thrombospondin stimulates motility of human neutrophils," *J. Cell. Biol.* 111:3077, 1990.

Naldini, Carney, Bocci, Klimpel, Asuncion, Soares and Klimpel, "Thrombin enhances Tcell proliferative responses and cytokine production," *Cell Immunol.* 147:367, 1993.

Perez-Rodriguez, Franchi and Pouyssegur, "Growth factor requirements of Chinese hamster lung fibroblasts in serum-free media: High mitogenic reaction of thrombin," *Cell Biol. Int. Rep.* 5:347, 1981.

Rasmussen, Craviari, Jallat, Schlesinger, Pages, Pavirani, Lecocq, Pouyssegur and Van Obberghen-Shilling, "cDNA cloning and expression of a hamster thrombin receptor coupled to $CA^{+2}$ mobilization," *FEBS Letters* 288:123, 1991.

Stiernberg, Redin, Warner and Carney, "The role of thrombin and thrombin receptor activating peptide (TRAP-508) in initiation of tissue repair," *Thrombosis and Haemostasis* 70:158. 1993.

Thomas, Hedrick, Smith, Pang, Jerome, Willard and Shirley, "Superoxide generation by the human polymorphonuclear_eukocytes in response to latex beads," J. Leukoc. Biol. 51:591, 1992.

Van Obberghen-Schilling and Pouyssegur, "Alpha-thrombin receptors and growth signaling." *Semin. Thromb. Hemos.* 19:378, 1993.

Vu, Hung, Wheaton and Coughlin. "Molecular cloning of a functional thrombin receptor reveals a novel proteolytic mechanism of receptor activation," *Cell* 64:1057, 1991.

Zong, Hayzer, Corson and Runge, "Molecular cloning of the rat vascular smooth muscle thrombin receptor: Evidence for in vitro regulation by basic fibroblast growth factor," *J. Biol. Chem.* 265:16975, 1992.

---

What is claimed is:

1. A polypeptide wherein said polypeptide consists of the amino acid sequence of SEQ ID NO. 1, SEQ ID NO. 2, SEQ ID NO. 3, or SEQ ID NO. 4, or consists of a fragment of SEQ ID NO. 1, SEQ ID NO. 2, SEQ ID NO. 3, or SEQ ID NO. 4, wherein said fragment consists of at least seven amino acids and said fragment is chemotactic.

2. A polypeptide consisting of the amino acid sequence of SEQ ID NO. 1.

* * * * *